(12) United States Patent
Takahashi

(10) Patent No.: US 11,980,490 B2
(45) Date of Patent: May 14, 2024

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventor: Naoto Takahashi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 239 days.

(21) Appl. No.: 17/529,922

(22) Filed: Nov. 18, 2021

(65) Prior Publication Data

US 2022/0160316 A1 May 26, 2022

(30) Foreign Application Priority Data

Nov. 25, 2020 (JP) ................................. 2020-194819

(51) Int. Cl.
*A61B 6/00* (2006.01)
*A61B 6/42* (2024.01)
*H04N 5/32* (2023.01)

(52) U.S. Cl.
CPC ............ *A61B 6/4291* (2013.01); *A61B 6/482* (2013.01); *H04N 5/32* (2013.01)

(58) Field of Classification Search
CPC ..... A61B 6/4291; A61B 6/482; A61B 6/5258; H04N 5/32; G06T 2207/10116; G06T 5/005; G06T 5/10; G06T 11/005
See application file for complete search history.

(56) References Cited

U.S. PATENT DOCUMENTS

2016/0235384 A1\* 8/2016 Enomoto ............. A61B 6/4291

FOREIGN PATENT DOCUMENTS

| JP | 2001212139 A | 8/2001 |
| JP | 2002330342 A | 11/2002 |
| JP | 2014150844 A | 8/2014 |

\* cited by examiner

*Primary Examiner* — Courtney D Thomas
(74) *Attorney, Agent, or Firm* — CANON U.S.A., INC. IP Division

(57) ABSTRACT

An image processing apparatus removes a pattern caused by a grid from a radiation image captured by using a scattered ray removal grid. The image processing apparatus includes a grid pattern removal unit, a filtering unit, and a distortion correction unit. The grid pattern removal unit is configured to generate a grid pattern removal image by removing a grid pattern from the radiation image. The filtering unit is configured to extract a frequency component lower than a frequency of the grid pattern from the radiation image. The distortion correction unit is configured to replace a low-frequency component included in the grid pattern removal image with a frequency component obtained by the filtering unit.

14 Claims, 9 Drawing Sheets

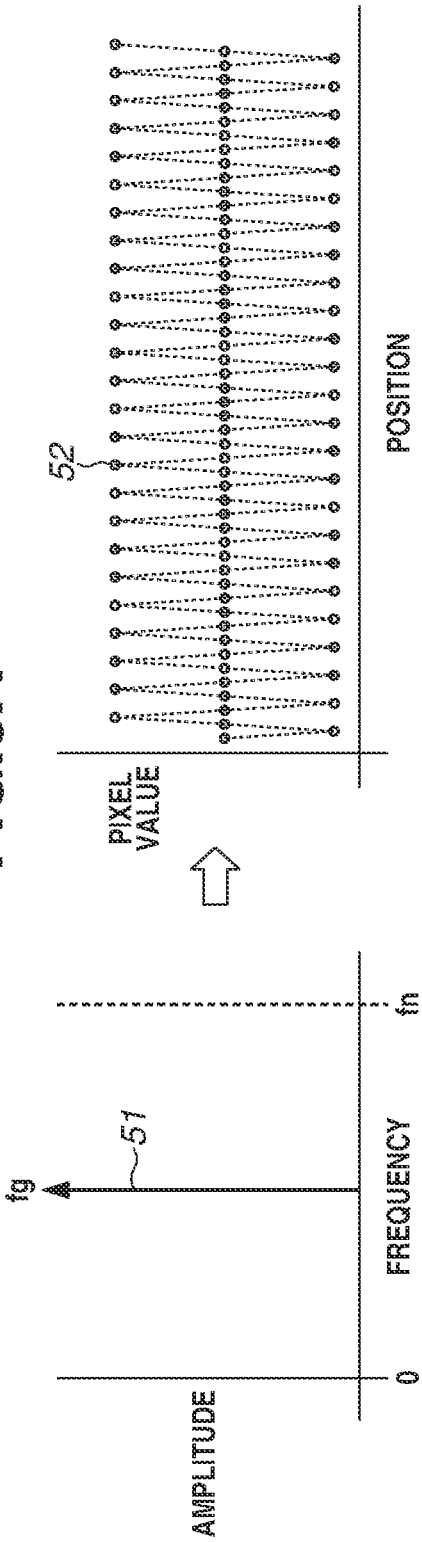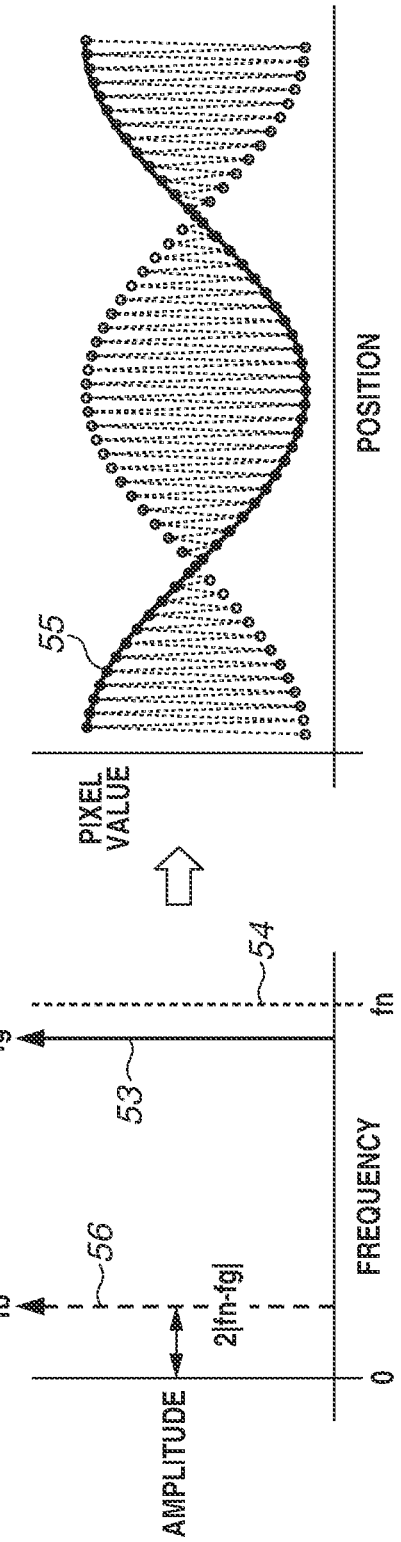

IMAGE PROCESSING APPARATUS, IMAGE PROCESSING METHOD, AND STORAGE MEDIUM

BACKGROUND

Technical Field

One disclosed aspect of the embodiments relates to an image processing apparatus, an image processing method, and a storage medium.

Description of the Related Art

A technique of irradiating an object with radiation represented by an X-ray and imaging the radiation transmitted through the object with a flat panel detector (hereinafter, referred to as an FPD) has been used in a medical field.

The radiation generates scattered rays inside the object, and therefore an instrument called a grid for removing the scattered rays may be disposed between the object and the FPD to perform imaging.

The grid is formed by alternately arranging a radiation shielding substance, such as lead, and a radiation transmission substance, such as aluminum or carbon, with a predetermined width to remove the scattered rays. However, the grid may generate a periodic signal (also referred to as a grid pattern) on an image and may disturb an observer.

Japanese Patent Application Laid-Open No. 2001-212139 discusses a method of limiting a condition of a grid to be used such that a grid pattern does not disturb an observer. Japanese Patent Application Laid-Open No. 2002-330342 also discusses a method of actively removing a generated grid pattern.

Meanwhile, Japanese Patent Application Laid-Open No. 2001-212139 uses a grid that does not generate a beat that makes an observer to have the strongest sense of incongruity. The beat is a low-frequency fluctuation appearing in real space, which will be described below in detail. However, some facilities have a need to use the same grid for a plurality of FPDs having different sampling pitches, and it may not be capable of satisfying a condition in which no beat occurs for all the FPDs.

The method discussed in Japanese Patent Application Laid-Open No. 2002-330342 removes only a periodic signal caused by a grid, and can accurately remove only a grid pattern without deteriorating an object signal as compared with typical filtering. However, under a condition where a beat occurs, a low-frequency periodic signal caused by nonlinearity of processing may occur. The occurring low-frequency periodic signal is a phenomenon called intermodulation distortion. The low-frequency periodic signal has a frequency twice a difference between a Nyquist frequency of the image and a frequency of a grid pattern, and the low-frequency periodic signal is superimposed on an image as a periodic signal, which may hinder observation. That is, a grid pattern cannot be effectively removed in some cases.

SUMMARY

One aspect of the embodiments has been made to solve the above-described issues, and is directed to a method of effectively removing a grid pattern.

According to an aspect of the embodiments, an image processing apparatus removes a pattern caused by a grid from a radiation image captured by using a scattered ray removal grid. The image processing apparatus includes a grid pattern removal unit, a filtering unit, and a distortion correction unit. The grid pattern removal unit is configured to generate a grid pattern removal image by removing a grid pattern from the radiation image. The filtering unit is configured to extract a frequency component lower than a frequency of the grid pattern from the radiation image. The distortion correction unit is configured to replace a low-frequency component included in the grid pattern removal image with a frequency component obtained by the filtering unit.

Further features of the disclosure will become apparent from the following description of exemplary embodiments with reference to the attached drawings.

BRIEF DESCRIPTION OF THE DRAWINGS

FIGS. 5A and 5B are schematic diagrams illustrating how a beat occurs.

DESCRIPTION OF THE EMBODIMENTS

Hereinafter, preferred exemplary embodiments will be described with reference to the accompanying drawings.

A radiographic apparatus according to a first exemplary embodiment corrects, by using a frequency component in which no intermodulation distortion occurs, intermodulation distortion that occurs when a grid pattern is removed, and removes the grid pattern.

Figure 1:
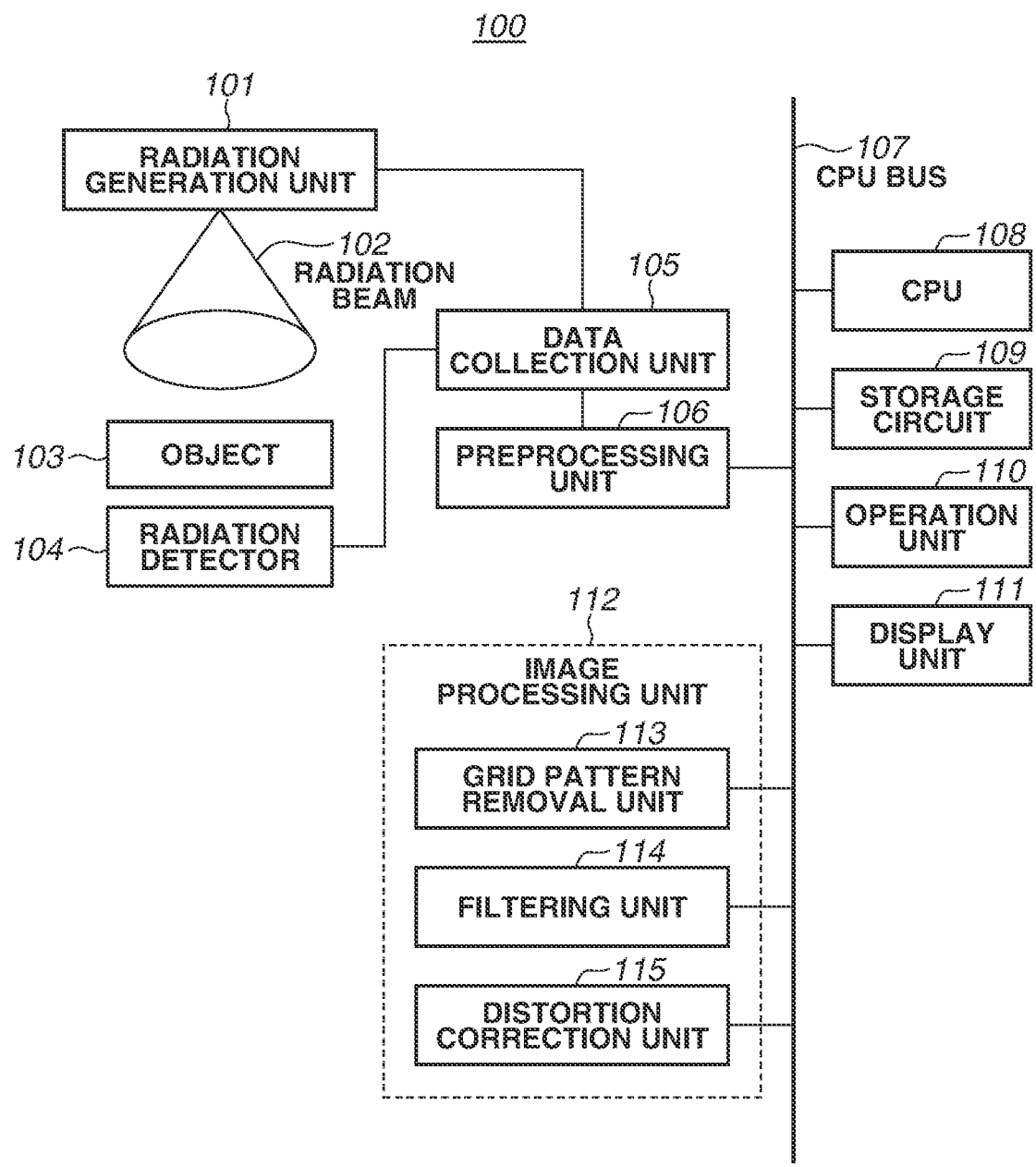
FIG. 1 is a configuration diagram of an entire radiographic apparatus according to a first exemplary embodiment.

The radiographic apparatus according to the present exemplary embodiment is implemented as, for example, a radiographic apparatus 100 as illustrated in FIG. 1. That is, the radiographic apparatus 100 is a radiographic apparatus having an image processing function of removing a grid pattern from a radiation image obtained by radiographic imaging. The radiographic apparatus 100 includes a radiation generation unit 101, a radiation detector 104, a data collection unit 105, a preprocessing unit 106, a central processing unit (CPU) 108, a storage circuit 109, an operation unit 110, a display unit, panel, or device 111, and an image processing unit 112. These units are connected via a CPU bus 107 to exchange data with each other. These units may be hardware devices, circuits, or functionalities, functions, modules or routines performed by a processor executing a program from a memory device. The processor may be any suitable processor that can execute a program, such as the CPU 108.

The image processing unit 112 removes a grid pattern from a radiation image captured by the radiation detector 104. The image processing unit 112 includes a grid pattern removal unit 113, a filtering unit 114, and a distortion correction unit 115.

In the radiographic apparatus 100 as described above, the storage circuit 109 stores various types of data used for processing executed in the CPU 108, and functions as a working memory of the CPU 108. The CPU 108 uses the storage circuit 109 to perform, for example, operation control of the entire apparatus according to an operation from the operation unit 110. With this configuration, the radiographic apparatus 100 operates as follows.

First, an operator selects one desired imaging protocol from a plurality of imaging protocols via the operation unit 110, whereby an imaging instruction is given to the apparatus. Here, the imaging protocol is a series of operation parameter sets used when a desired examination is performed. By creating a plurality of imaging protocols in advance, it is possible to easily set conditions according to the examination. As information regarding the imaging protocol, various settings are associated, such as an imaging region, imaging conditions (e.g., tube voltage, tube current, and irradiation time), presence or absence of a grid, grid specifications (e.g., focusing distance, lattice ratio, and grid density), and image processing parameters. In the present exemplary embodiment, a grid pattern is removed by using information regarding presence or absence of a grid and grid density associated with the imaging protocol. A method of removing a grid pattern will be described below.

As described above, the imaging instruction input by the operator is transmitted to the data collection unit 105 by the CPU 108. When receiving the imaging instruction, the CPU 108 controls the radiation generation unit 101 and the radiation detector 104 to execute radiographic imaging.

In the radiographic imaging, the radiation generation unit 101 first irradiates an object 103 with a radiation beam 102. The radiation beam 102 emitted from the radiation generation unit 101 is transmitted through the object 103 while being attenuated, and reaches the radiation detector 104. The radiation detector 104 then outputs a signal according to intensity of the reached radiation. Note that, in the present exemplary embodiment, the object 103 is a human body or a biological tissue. Thus, the signal output from the radiation detector 104 is data obtained by imaging the human body.

The data collection unit 105 converts the signal output from the radiation detector 104 into a predetermined digital signal, and supplies the digital signal as radiation image data to the preprocessing unit 106. The preprocessing unit 106 performs preprocessing, such as offset correction and gain correction, on the radiation image data supplied from the data collection unit 105. The radiation image data preprocessed by the preprocessing unit 106 is sequentially transferred to the storage circuit 109 and the image processing unit 112 via the CPU bus 107 under the control of the CPU 108.

The image processing unit 112 executes image processing of removing a grid pattern from the radiation image data.

The image processing unit 112 includes, as functional configurations thereof, the grid pattern removal unit 113, the filtering unit 114, and the distortion correction unit 115. The grid pattern removal unit 113 generates a grid pattern removal image by removing a grid pattern from the captured radiation image. The filtering unit 114 extracts a frequency component having a frequency lower than a frequency of the grid pattern, from the captured radiation image.

The distortion correction unit 115 corrects the grid pattern removal image by using the frequency component extracted by the filtering unit 114. The radiation image processed by the image processing unit 112 is displayed on the display unit 111, confirmed by the operator, and then output to, for example, a printer (not illustrated), and a series of imaging operations ends.

Figure 2:
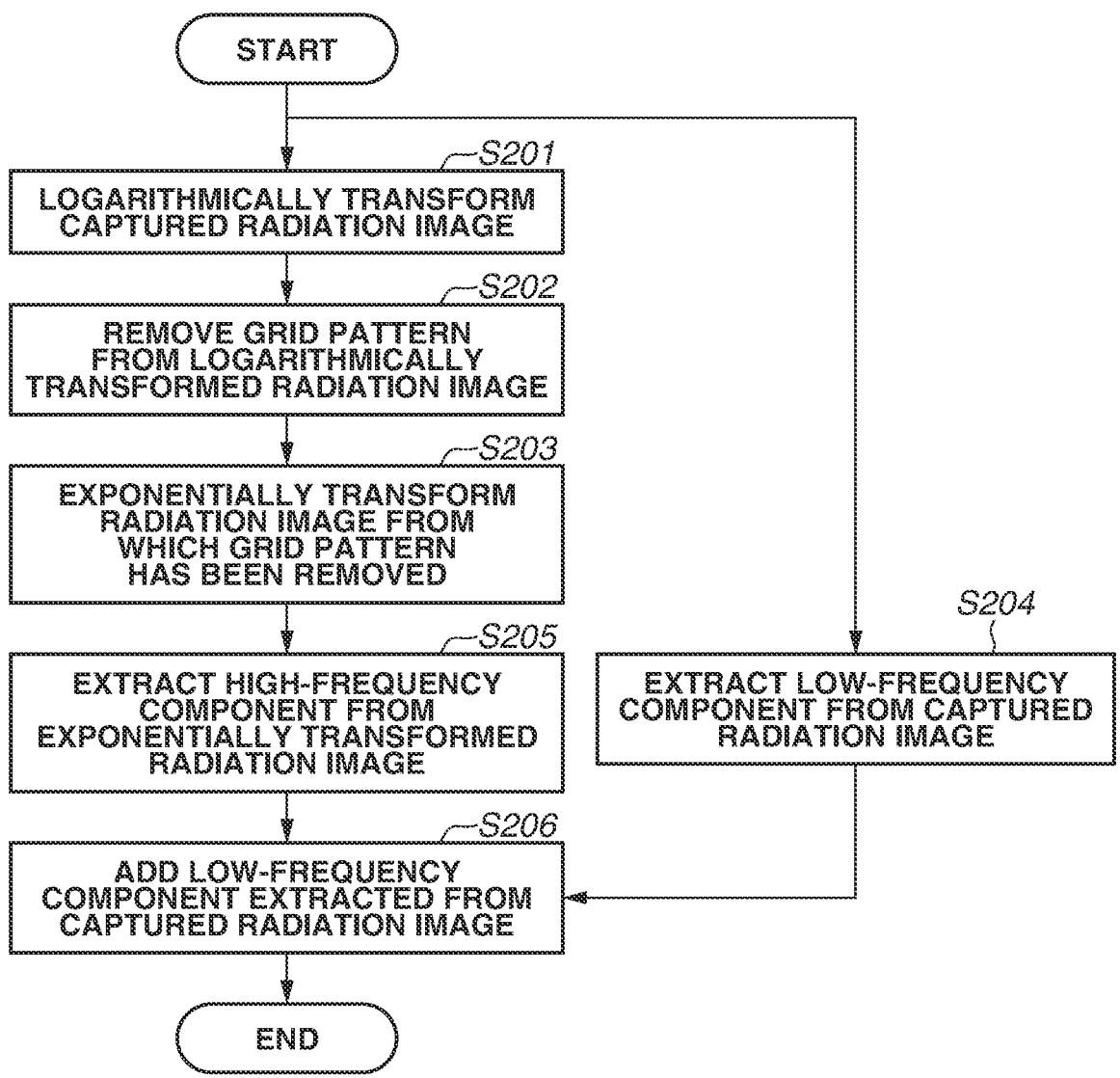
FIG. 2 is a flowchart illustrating a processing procedure of image processing according to the first exemplary embodiment.

The operation of the image processing unit 112, which is a characteristic of the present exemplary embodiment, i.e., the operation of removing the grid pattern from the captured radiation image in the radiographic apparatus 100 including the above-described configurations will now be specifically described with reference to a flowchart illustrated in FIG. 2.

The radiation image data obtained by the preprocessing unit 106 as described above is transferred to the image processing unit 112 via the CPU bus 107. The grid pattern removal unit 113 then executes each of steps S201 to S203 to remove the grid pattern.

Specifically, the method of Japanese Patent Application Laid-Open No. 2002-330342, which has already been discussed by the present applicant, is used. In such a method, a shade of a grid pattern superimposed substantially multiplicatively on an object signal is converted by logarithmic transformation into a signal additively superimposed. From the converted signal, only the grid pattern is separated and subtracted to remove the grid pattern.

(Step S201: Logarithmically Transforming Captured Radiation Image)

In step S201, the grid pattern removal unit 113 first converts an input image X, which is the radiation image captured by the radiographic apparatus 100 and has a pixel value proportional to a dose, into a pixel value proportional to a logarithm of the dose by the following equation (1), to convert the input image X into a form in which a shade of the grid pattern is additively superimposed.

$$Y = \begin{cases} \log_{10}(X), & X \geq 1 \\ 0, & \text{otherwise} \end{cases} \qquad (1)$$

(Step S202: Removing Grid Pattern from Logarithmically Transformed Radiation Image)

In step S202, the grid pattern removal unit 113 extracts the grid pattern from the radiation image obtained by converting the pixel value proportional to the dose into the pixel value proportional to the logarithm of the dose in step S201, and subtracts the extracted grid pattern to remove the grid pattern. That is, the grid pattern removal unit 113 corresponds to an example of a grid pattern removal unit that generates a grid pattern removal image from a radiation image having a pixel value proportional to a logarithm of a dose.

Specifically, the grid pattern removal unit 113 roughly extracts the grid pattern by using a finite impulse response (FIR) filter based on a frequency fg of the grid pattern, and then estimates and repairs the grid pattern. Since details are known from Japanese Patent Application Laid-Open No. 2002-330342, description thereof is omitted here. The frequency of the grid pattern described above is determined based on the density of a grid to be used and a sampling pitch (referred to also as a pixel pitch) of a sensor. Specifically, the frequency fg [rad/sample] of the grid can be obtained by the following equation (2).

$$f_g = 2\pi \cdot \left| \frac{D \cdot S}{10} - n \right|, \qquad (2)$$

where D [lines/cm] is the density of the grid to be used, S [mm] is the sampling pitch, and n is an integer satisfying the following inequality (3).

$$0 \le f_g \le \pi \quad (3)$$

(Step S203: Exponentially Transforming Radiation Image from which Grid Pattern has Been Removed)

In step S203, the grid pattern removal unit 113 converts a pixel value of an image Y from which the grid pattern has been removed into a value proportional to the dose. Specifically, it is sufficient that inverse transformation of the logarithmic transformation is performed by the following equation.

$$X = 10^Y.$$

As described above, the radiation image from which the grid pattern has been removed is generated.

Next, correction of intermodulation distortion, which is a characteristic of the present exemplary embodiment, is performed on the radiation image from which the grid pattern has been removed. Here, the intermodulation distortion is a phenomenon in which a beat that is not a real image becomes a real image by processing with strong nonlinearity.

Figure 6A:
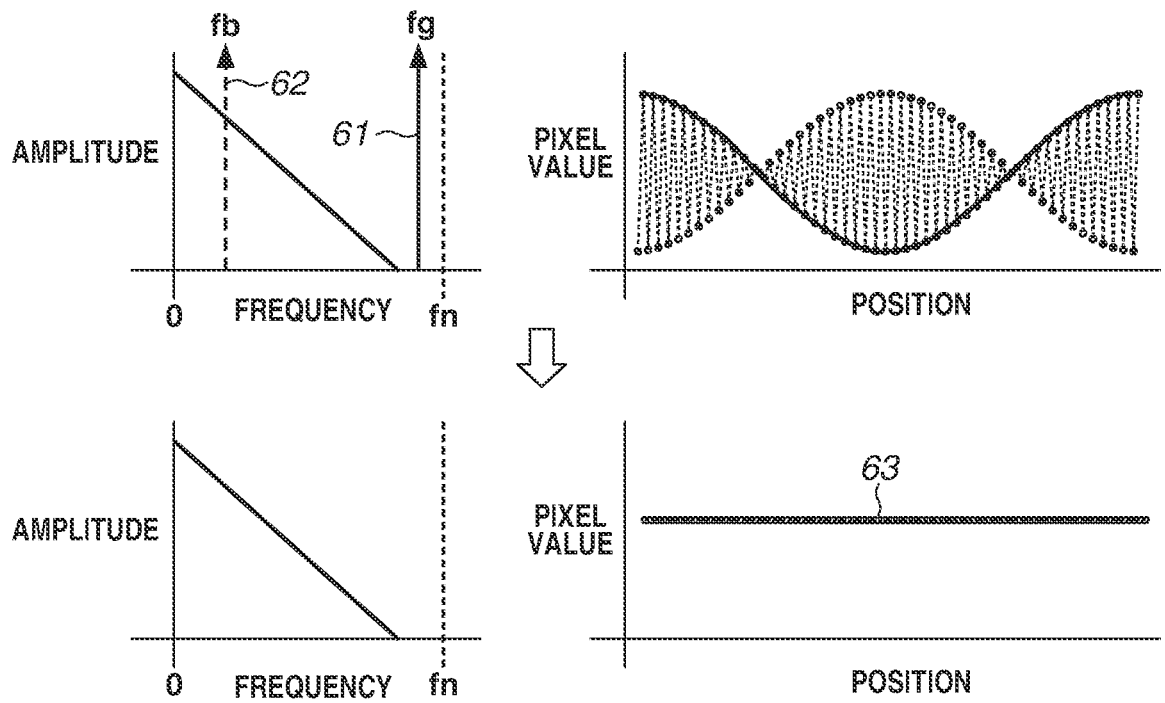
FIGS. 6A and 6B are schematic diagrams illustrating how intermodulation distortion occurs.
Figure 6B:
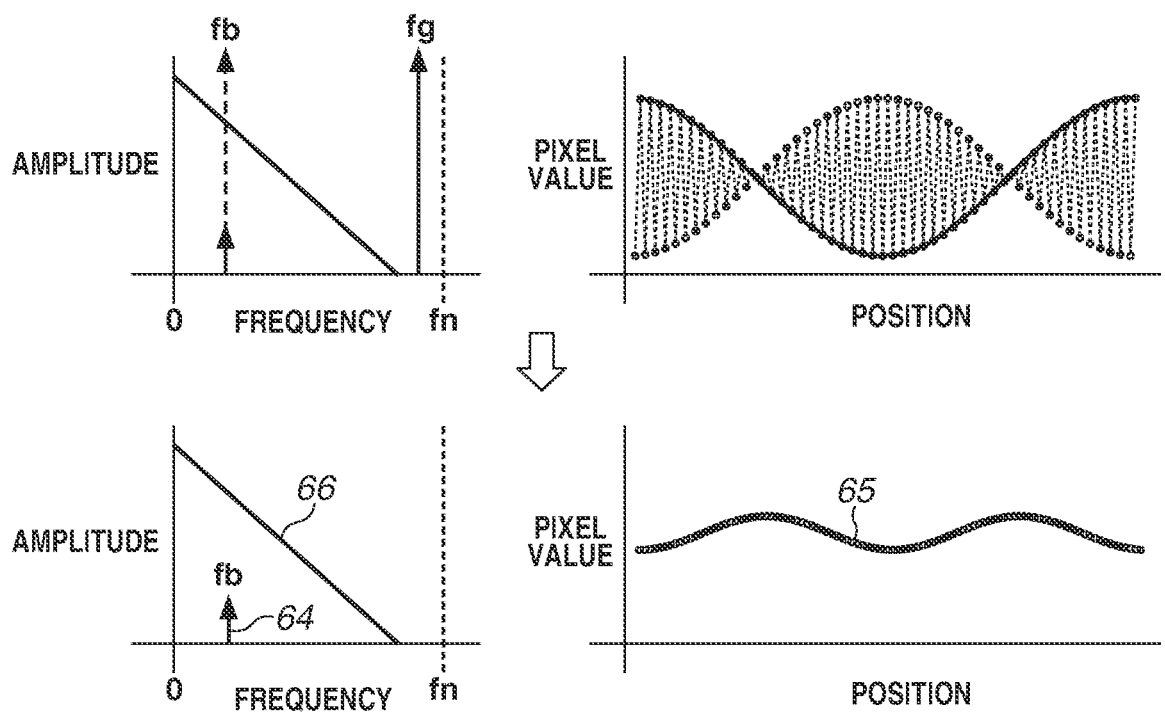

The phenomenon will be described with reference to FIGS. 5A to 6B. FIGS. 5A and 5B illustrate how a beat occurs, and FIGS. 6A and 6B illustrate how intermodulation distortion occurs. For example, a reference sign 51 illustrated in FIG. 5A represents a grid pattern on a frequency axis. As illustrated in the drawing, the grid pattern is a substantially line spectrum component having a peak at a position of the frequency fg. The grid pattern appears as a substantially single frequency signal as indicated by a reference sign 52 in real space. In contrast, in a case where a beat occurs, a low-frequency fluctuation appears in real space separately from a single frequency signal, as indicated by a reference sign 55. This fluctuation is called a beat.

Here, a condition where a beat occurs is a case where the frequency fg of the grid indicated by a reference sign 53 is close to a Nyquist frequency fn indicated by a reference sign 54. Specifically, as discussed in Japanese Patent Application Laid-Open No. 2001-212139, a beat remarkably appears when the frequency fg of the grid is 80% or more of the Nyquist frequency fn. Note that the frequency fb of this beat is 2×|fn−fg|, but the beat is a virtual image with no substance. Thus, even a signal in which a beat occurs does not show a line spectrum at a position of a frequency fb of the beat indicated by a reference sign 56 on the frequency axis.

FIGS. 6A and 6B illustrate a signal change in a case where a grid pattern is removed under the condition where a beat occurs. FIG. 6A illustrates an ideal state in which no intermodulation distortion occurs. As described above, the beat is not a real image but a virtual image caused by a grid pattern. Thus, when a grid pattern 61, which is a factor that generates a beat, is removed, a low-frequency fluctuation due to the beat is also removed together with the grid pattern as indicated by a reference sign 63 in a signal in real space. However, in a case where the removal of the grid pattern is processing with strong nonlinearity, a phenomenon illustrated in FIG. 6B occurs.

Specifically, in a case where the grid pattern is removed, a part of the low-frequency fluctuation, which is a virtual image, becomes a real image and appears as a line spectrum also on a frequency axis as indicated by a reference sign 64. In such a case, as indicated by a reference sign 65, the low-frequency fluctuation that should originally disappear remains also in real space. Thereby, there is a case where observation is hindered.

Since such a fluctuation is superimposed on a low frequency that is a main signal component with respect to a spectrum 66 of an object signal, it is difficult to separate the fluctuation from the object signal after the superimposition. In the present exemplary embodiment, a low-frequency component is therefore extracted from a radiation image before intermodulation distortion is superimposed on a low frequency, and the distortion is corrected. A specific method will be described below with reference to the flowchart in FIG. 2.

(Step S204: Extracting Low-Frequency Component from Captured Radiation Image)

In step S204, the filtering unit 114 extracts a low-frequency component from the radiation image before the intermodulation distortion occurs, that is, the radiation image from which the grid pattern has not been removed. That is, the filtering unit 114 extracts a frequency component lower than the frequency of the grid pattern from the radiation image having the pixel value proportional to the dose. Here, a linear low-pass filter is applied to the radiation image before the logarithmic transformation, which is nonlinear processing, to extract a low-frequency component. The filter to be used for the extraction may be any filter having characteristics in which the frequency of the grid pattern is included in a stopband and the frequency of the beat generated by the grid pattern is included in a passband.

Figure 7:
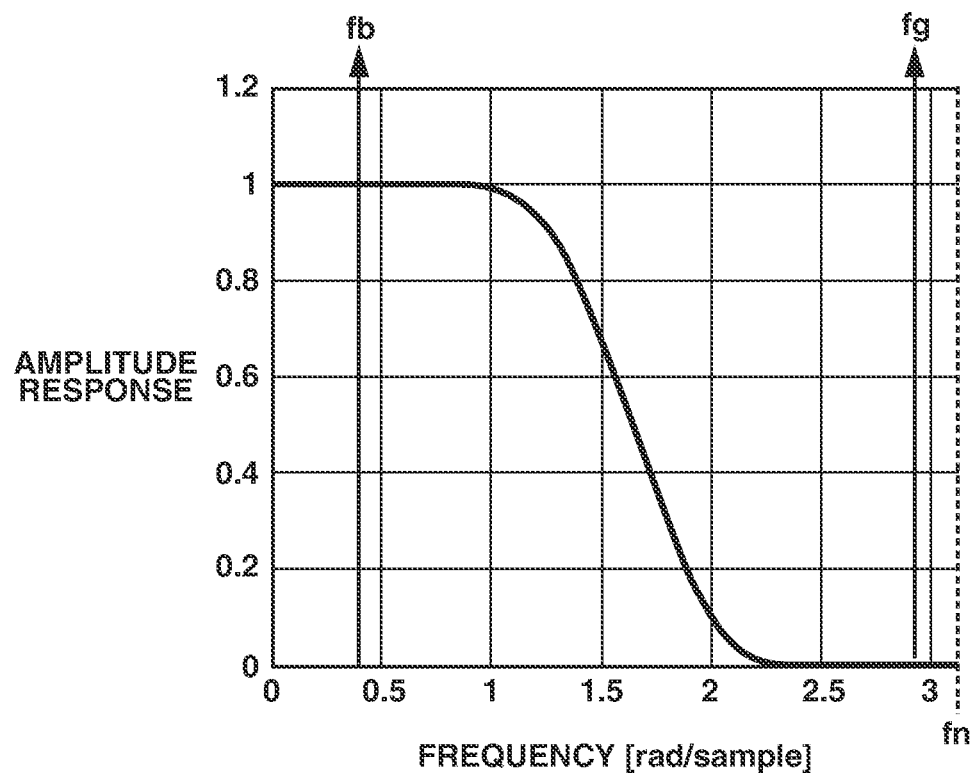
FIG. 7 illustrates an example of characteristics of a low-pass filter.

Specifically, for example, it is sufficient to use a filter having characteristics in which an amplitude response is 1 at the frequency fb of the intermodulation distortion and the amplitude response is 0 at the frequency fg of the grid, and filtering is performed by using a filter having characteristics as illustrated in FIG. 7. That is, for example, the filtering unit 114 performs filtering by using a filter having characteristics in which at least the amplitude response is 0 at fg and the amplitude response is 1 at 2×(fn−fg), where fn is the Nyquist frequency and fg (satisfying fg≤fn) is the frequency of the grid pattern.

(Step S205: Extracting High-Frequency Component from Exponentially Transformed Radiation Image)

Figure 8:
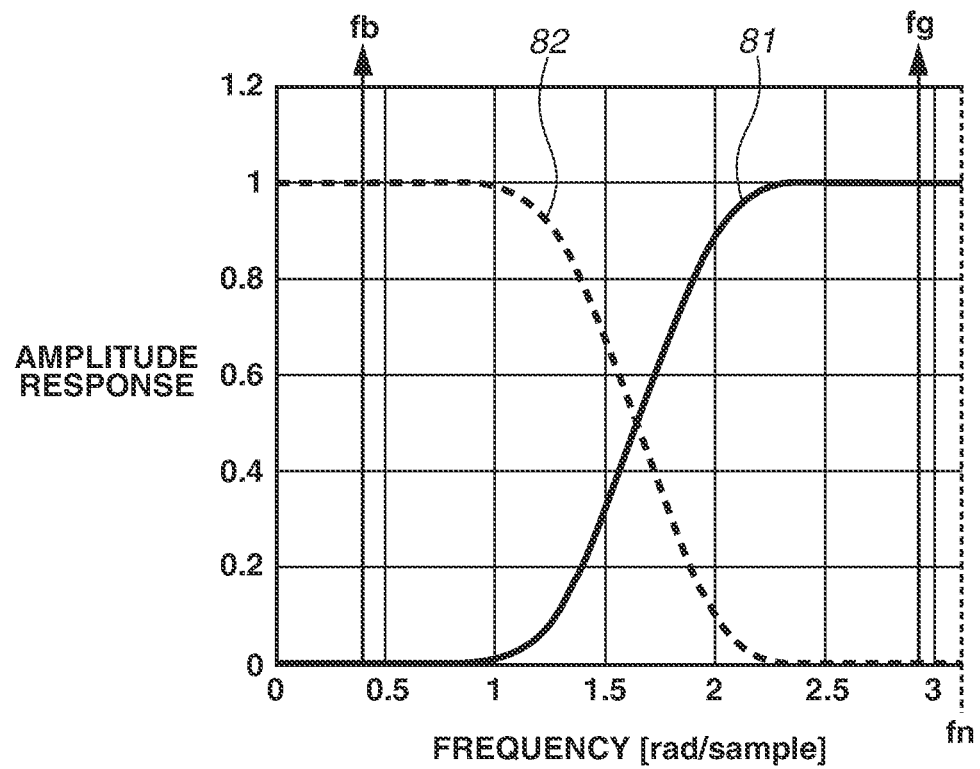
FIG. 8 illustrates an example of characteristics of a high-pass filter.

In step S205, the distortion correction unit 115 removes the low-frequency component in which intermodulation distortion occurs from the radiation image from which the grid pattern has been removed, and extracts a high-frequency component. Specifically, a linear high-pass filter is applied to remove the low-frequency component. Here, filtering is performed by using, as the high-pass filter, a filter having characteristics indicated by a reference sign 81 exactly opposite to characteristics 82 of the low-pass filter used in the filtering unit 114 as illustrated in FIG. 8.

A filter coefficient Hpf of this high-pass filter can be calculated by the following equation (4).

$$Hpf[i] = \begin{cases} 1 - Lpf[i], & i = N/2 \\ -Lpf[i], & \text{otherwise} \end{cases}, i = 0, 1, \ldots, N, \quad (4)$$

where Lpf is a filter coefficient of the low-pass filter used in the filtering unit 114, and N represents a filter order and is an even number of 2 or more.

(Step S206: Adding Low-Frequency Component Extracted from Captured Radiation Image)

Figure 9:
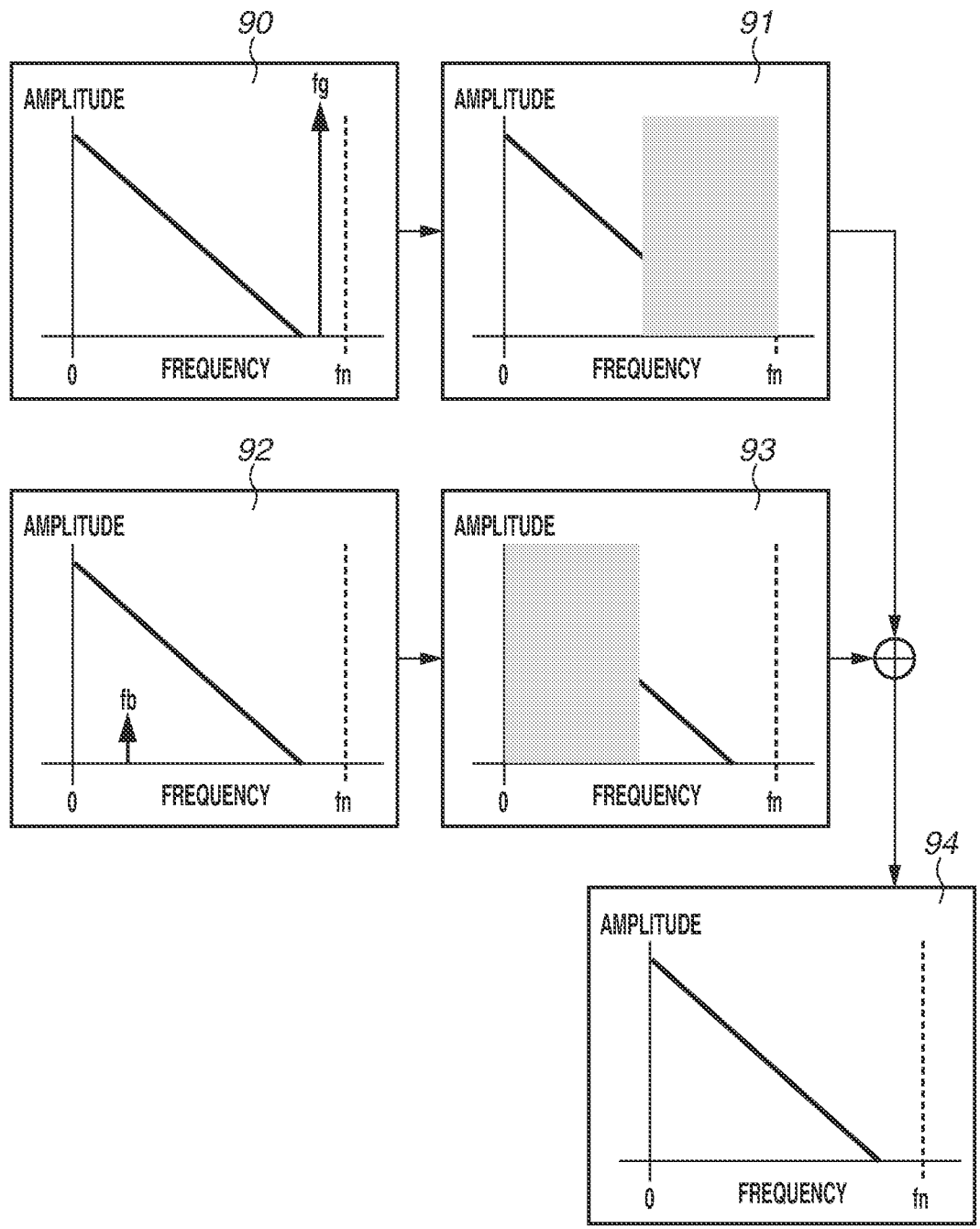
FIG. 9 is a diagram for describing distortion correction.

In step S206, the distortion correction unit 115 adds the low-frequency component extracted by the filtering unit 114 to the radiation image from which the low-frequency component has been removed and the high-frequency component has been extracted to correct the distortion. FIG. 9 is a diagram illustrating a process of the distortion correction, on a frequency axis. A reference sign 90 indicates the captured radiation image, and a line spectrum appears at the position of the frequency fg of the grid as illustrated in the drawing. In contrast, an image 91 is a result of extracting the low-frequency component by the filtering unit 114. In the image 91, a grid pattern has been removed, and an object signal present at a high frequency has also been removed. In contrast, a reference sign 92 indicates a radiation image from which a grid pattern has been removed. In this radiation image, only a grid pattern is removed without removing an object signal, but a line spectrum due to intermodulation distortion occurs at fb. An image 93 is a result of extracting the high-frequency component from the radiation image. In this case, intermodulation distortion has been removed, and an object signal present at a low frequency has also been removed. In both the images 91 and 93, a part of the object signal is removed, but filter characteristics used for filtering are exactly opposite characteristics. Thus, the removed object signals are complemented with each other if the images 91 and 93 are added. In other words, the sum of an amplitude response of a filter that extracts the high-frequency component and an amplitude response of a filter used by the filtering unit 114 to extract the low-frequency component is 1 at all frequencies. As a result, the object signal can completely be reproduced as in an image 94, and both the grid pattern and the intermodulation distortion can be removed, accordingly.

As described above, in the first exemplary embodiment, it is possible to remove the grid pattern and the intermodulation distortion without deteriorating the object signal by adding the low-frequency component extracted from the captured radiation image and the high-frequency component extracted from the radiation image from which the grid pattern has been removed. Whereby there is an effect of improving image quality.

In the first exemplary embodiment, a configuration is adopted in which the high-frequency component is extracted, by using the high-pass filter, from the radiation image from which the grid pattern has been removed, and the low-frequency component in which the intermodulation distortion occurs is replaced with the high-frequency component. However, the disclosure is not limited to this configuration.

For example, the same low-pass filter as the filter used by the filtering unit 114 can be used. Specifically, similar processing can be performed by the following equation.

$$O = (I - Lpf * I) + L,$$

where I is the radiation image from which the grid pattern has been removed, L is the low-frequency component extracted by the filtering unit 114, Lpf is the low-pass filter used by filtering unit 114, and * represents convolution.

That is, a configuration may be adopted in which the low-frequency component extracted from the image from which the grid pattern has been removed by using the same filter as the filter used by the filtering unit 114 is replaced with the low-frequency component extracted by the filtering unit 114. In particular, the distortion may be corrected by subtracting the low-frequency component extracted from the image from which the grid pattern has been removed from the image from which the grid pattern has been removed, and adding the low-frequency component extracted by the filtering unit to the image from which the low-frequency component has been subtracted.

As described above, the grid pattern can be effectively removed even under the condition where a beat occurs, by replacing the intermodulation distortion that occurs when the grid pattern is removed with the frequency component in which no intermodulation distortion occurs.

The processing in steps S204 to S206 in the present exemplary embodiment may be performed in a case where a relationship of $0.8 \times fn \leq fg$ is satisfied, where fn is the Nyquist frequency of the radiation image, fg (satisfying $fg \leq fn$) is the frequency of the grid pattern.

Figure 3:
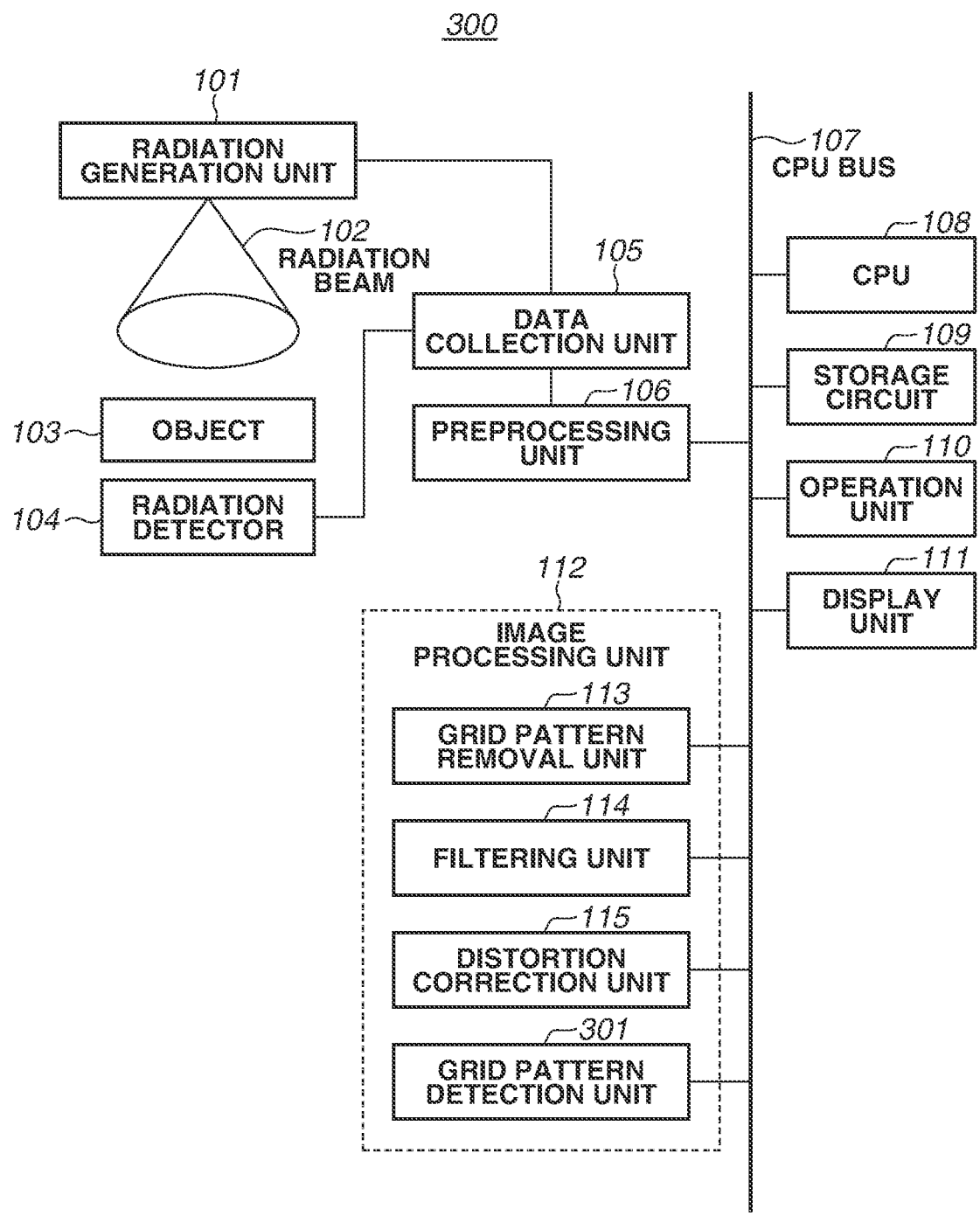
FIG. 3 is a configuration diagram of an entire radiographic apparatus according to a second exemplary embodiment.
Figure 4:
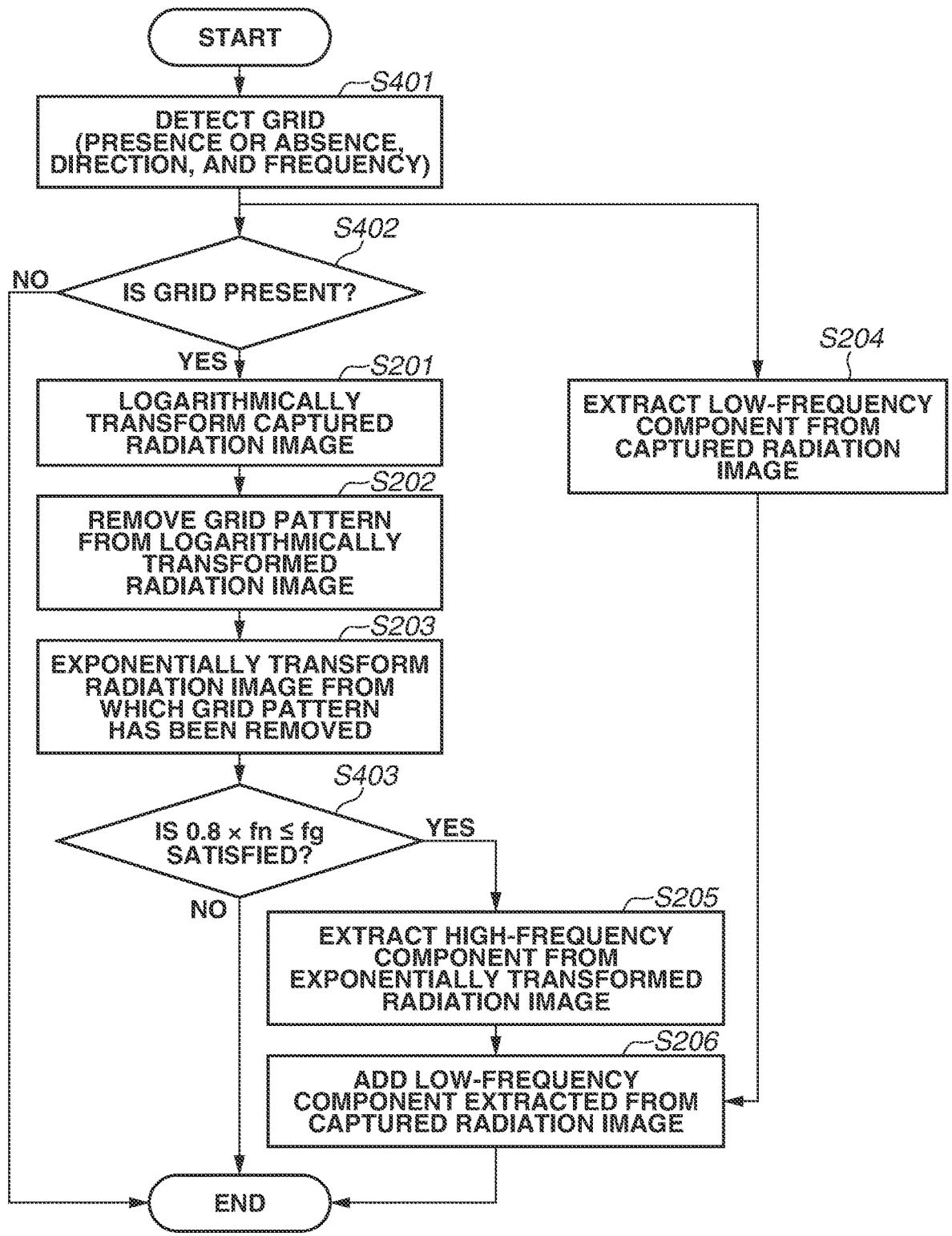
FIG. 4 is a flowchart illustrating a processing procedure of image processing according to the second exemplary embodiment.

A second exemplary embodiment is applied to a radiographic apparatus 300 illustrated in FIG. 3, for example. The radiographic apparatus 300 includes a grid pattern detection unit 301 in addition to the radiographic apparatus 100. With this configuration, there is a function of automatically performing execution control of processing according to presence or absence of a grid pattern and a frequency, in addition to the operation in the first exemplary embodiment. A method of the execution control of the processing, which is an operation different from that of the first exemplary embodiment, will now be described with reference to a flowchart illustrated in FIG. 4.

(Step S401: Detecting Grid)

In step S401, the grid pattern detection unit 301 calculates presence or absence, a direction, and a frequency of a grid from a captured radiation image. For detection of a grid pattern, a method discussed in Japanese Patent Application Laid-Open No. 2014-150844, which has already been filed by the present applicant, is used. This method compares a grid pattern by comparing power spectra in a predetermined measurement region. Since details are known in Japanese Patent Application Laid-Open No. 2014-150844, description thereof is omitted here.

(Step S402: Is Grid Present?)

In step S402, the grid pattern detection unit 301 determines presence or absence of the grid from the captured radiation image. In a case where the grid is present (YES in step S402), the processing proceeds to steps S201 to S203. In steps S201 to S203, operations are executed in the grid pattern removal unit 113 to remove the grid pattern.

In a case where the grid is absent (NO in step S402), it is not necessary to remove the grid pattern, and thus the processing is terminated.

(Step S403: Is $0.8 \times fn \leq fg$ Satisfied?)

In step S403, if the result of the determination in step S402 indicates that the grid is present, and after the operations in steps S201 to S203 are executed, the grid pattern detection unit 301 determines whether a frequency fg of the grid is 80% of a Nyquist frequency fn or higher. That is, it is determined whether $0.8 \times fn \leq fg$ is satisfied.

If $0.8 \times fn \leq fg$ is satisfied and there is a possibility that intermodulation distortion occurs (YES in step S403), operations in steps S204 to S206 are executed to correct the intermodulation distortion. That is, the distortion is corrected if the relationship of $0.8 \times fn \leq fg$ is satisfied, where fn is the Nyquist frequency of the radiation image and fg (satisfying $fg \leq fn$) is the frequency of the grid pattern.

If the frequency fg of the grid does not satisfy the above-described condition (NO in step S403), no intermodulation distortion occurs. The operations in steps S204 to S206 are therefore skipped and the processing is completed.

That is, the distortion correction unit 115 switches whether to correct the distortion based on the detection result of the grid pattern detection unit 301.

As described above in the second exemplary embodiment, since the processing is not executed in a case where there is no grid, there is an effect that a possibility of deteriorating an object signal can be eliminated if there is no grid. Since only necessary processing is executed according to presence or absence of the grid and the frequency of the grid, an unnecessary increase in processing time can be suppressed.

As described above, according to an exemplary embodiment, a grid pattern can be effectively removed.

OTHER EMBODIMENTS

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-194819, filed Nov. 25, 2020, which is hereby incorporated by reference herein in its entirety.

What is claimed is:

1. An image processing apparatus comprising:
a grid pattern removal unit configured to generate a grid pattern removal image by removing a grid pattern from a radiation image captured by using a grid;
a filtering unit different from the grid pattern removal unit, configured to extract a frequency component lower than a frequency of the grid pattern from the radiation image; and
a correction unit configured to correct the grid pattern removal image generated by the grid pattern removal unit by using the frequency component extracted by the filtering unit.

2. The image processing apparatus according to claim 1, wherein the grid pattern removal unit generates a grid pattern removal image from a radiation image having a pixel value proportional to a logarithm of a dose.

3. The image processing apparatus according to claim 1, wherein the filtering unit extracts a frequency component lower than a frequency of a grid pattern from a radiation image having a pixel value proportional to a dose.

4. The image processing apparatus according to claim 1, wherein the correction unit corrects distortion by adding a low-frequency component extracted by the filtering unit to a high-frequency component extracted by filtering from the grid pattern removal image.

5. The image processing apparatus according to claim 4, wherein a sum of an amplitude response of a filter that extracts the high-frequency component and an amplitude response of a filter used by the filtering unit is 1 at all frequencies.

6. The image processing apparatus according to claim 1, wherein the correction unit replaces a low-frequency component extracted from the grid pattern removal image by using the same filter as a filter of the filtering unit with a low-frequency component extracted by the filtering unit.

7. The image processing apparatus according to claim 6, wherein the correction unit corrects distortion by subtracting the low-frequency component extracted from the grid pattern removal image from the grid pattern removal image, and adding the low-frequency component extracted by the filtering unit to the grid pattern removal image from which the low-frequency component has been subtracted.

8. The image processing apparatus according to claim 1, wherein the filtering unit performs filtering by using a filter having characteristics in which the frequency of the grid pattern is included in a stopband and a frequency of a beat generated by the grid pattern is included in a passband.

9. The image processing apparatus according to claim 8, wherein, in a case where a Nyquist frequency of the radiation image is fn and the frequency of the grid pattern is fg (satisfying fg≤fn), the filtering unit performs filtering by using a filter having characteristics in which at least an amplitude response is 0 at fg and the amplitude response is 1 at 2×(fn−fg).

10. The image processing apparatus according to claim 1, wherein the correction unit corrects distortion in a case where a relationship of 0.8×fn≤fg is satisfied, where fn is a Nyquist frequency of the radiation image and fg (satisfying fg≤fn) is the frequency of the grid pattern.

11. The image processing apparatus according to claim 1, further comprising
a grid pattern detection unit configured to detect a frequency of a grid from the radiation image,
wherein the correction unit switches whether to correct distortion based on a detection result of the grid pattern detection unit.

12. A storage medium storing a program for causing a computer to function as each unit of the image processing apparatus according to claim 1.

13. An image processing system comprising:
a radiation detection apparatus that detects radiation; and
the image processing apparatus according to claim 1,
wherein the image processing apparatus is communicatively connected to the radiation detection apparatus.

14. An image processing method comprising:
generating a grid pattern removal image by removing a grid pattern from a radiation image captured by using a grid;
extracting, different from the generating, a frequency component lower than a frequency of the grid pattern from the radiation image; and correcting the grid pattern removal image generated in the generating by using the frequency component extracted in the extraction.

\* \* \* \* \*